United States Patent [19]

Etscorn et al.

[11] Patent Number: 5,674,496
[45] Date of Patent: Oct. 7, 1997

[54] ANIMAL REPELLENT

[75] Inventors: Frank T. Etscorn, Meeteetse, Wyo.; Lorenzo Torres, Magdalena, N. Mex.

[73] Assignee: New Mexico Tech Research Foundation, Socorro, N. Mex.

[21] Appl. No.: 139,432

[22] Filed: Oct. 20, 1993

[51] Int. Cl.$^6$ ............................................. A01N 65/00
[52] U.S. Cl. .......................... 424/195.1; 424/DIG. 10; 210/633
[58] Field of Search ................... 210/633, 767, 210/768, 774, 772, 790; 424/195.1, DIG. 10

[56] References Cited

U.S. PATENT DOCUMENTS

| | | | |
|---|---|---|---|
| 631,738 | 8/1899 | Dowie et al. | |
| 3,269,902 | 8/1966 | Goodhue et al. | 167/46 |
| 3,389,048 | 6/1968 | Kenaga | 167/46 |
| 3,434,995 | 3/1969 | Shotton | 260/31.2 |
| 3,683,090 | 8/1972 | Henry et al. | 424/293 |
| 3,857,934 | 12/1974 | Bernstein et al. | 424/30 |
| 3,864,468 | 2/1975 | Hyman et al. | 424/16 |
| 3,941,887 | 3/1976 | Hermann et al. | 424/322 |
| 4,097,607 | 6/1978 | Larson | 424/324 |
| 4,130,556 | 12/1978 | Wachter et al. | 424/195 |
| 4,169,898 | 10/1979 | Haase et al. | 424/331 |
| 4,171,463 | 10/1979 | Watkins | 174/120 R |
| 4,455,304 | 6/1984 | Yaralian | 424/195 |
| 4,496,467 | 1/1985 | Munteanu et al. | 252/92 |
| 4,501,736 | 2/1985 | Mitsuhashi et al. | 424/195 |
| 4,735,803 | 4/1988 | Katz et al. | 424/195.1 |
| 4,775,532 | 10/1988 | Clayton | 424/195.1 |
| 4,795,637 | 1/1989 | Harding, Jr. | 424/195.1 |
| 4,853,413 | 8/1989 | Katz et al. | 514/526 |
| 4,965,070 | 10/1990 | Messina | 424/581 |
| 5,002,768 | 3/1991 | Kondo et al. | 424/408 |
| 5,013,551 | 5/1991 | Atkinson | 424/412 |
| 5,226,380 | 7/1993 | Fischer | 114/222 |
| 5,229,119 | 7/1993 | Gutierrez Rigo | 424/195.1 |
| 5,277,910 | 1/1994 | Hidvegi | 424/195.1 |

FOREIGN PATENT DOCUMENTS

| | | |
|---|---|---|
| 0037829 | 11/1971 | Japan. |
| 0043906 | 12/1971 | Japan. |

OTHER PUBLICATIONS

Thresh "Capsaicin, The Active Principle of Capsicum Fruits" The Pharmaceutical Journal and Transactions p. 21 Jul. 1876.

Toh et al. "The Pharmacological Actions of Capsaicin and Analogues" Brit. J. Pharmacol. (1955) 10, 175, pp. 175–182.

Govindarajan et al., CRC Critical Reviews in Food Science and Nutrition, "Capsicum", pp. 207–288 (1986).

Andelt et al., "Effectiveness of capsaicin and bitrex repellents for deterring browsing by captive mule deer", Journal of Wildlife Management 58(2), 1994.

U.S. Environmental Protection Agency, "EPA R.E.D. FACTS—Capsaicin," Pub. 540/FS–92–219, pp. 1–4 (Jun., 1992).

U.S. Postal Service Specification for Dog Repellent, USPS–D–734A (re), pp. 1–11, Feb. 4, 1986.

Reese, K.M., "Hot Sauce Discourages Cable–Gnawing Animals," Newscripts—Chemical and Engineering News, May 21, 1990, p. 98.

B.R. Acord, "Animal Damage Control: Are We Prepared for the Next Century?" The Probe, Issue 111, Jun. 1991, pp. 1–5.

W.D. Fitzwater, "Bird Limes and Rat Glues—Sticky Situations," Proceedings of the Tenth Vertebrate Pest Conference, R.E. Marsh, Ed., University of California, Davis, Feb. 23 1982, pp. 17–20.

A.W. Logue, The Psychology of Eating and Drinking, W.H. Freeman and Company, Jan. 15, 1985 (p. 92).

Primary Examiner—Jeffrey Mullis
Attorney, Agent, or Firm—Deborah A. Peacock; Jeffrey D. Myers; Donovan F. Duggan

[57] ABSTRACT

A substance and method for minimizing or eliminating damage to objects caused by animals, especially gnawing and chewing rodents. A wide variety of objects and items can be protected by the practice of the invention. Methods are disclosed for extracting the active repellent ingredient from pepper plants, particularly habañero peppers, and for using the extract to treat the objects to be protected. Disclosed protective treatment methods include applying the extract directly to the item to be protected, and/or mixing the extract with caulks, paints, glues, or rubber coating materials.

85 Claims, No Drawings

ANIMAL REPELLENT

BACKGROUND OF THE INVENTION

1. Field of the Invention (Technical Field)

The invention relates to animal repellents, particularly rodent repellents. More particularly, the invention relates to compositions and methods of making and using compositions for repelling animals in order to minimize or prevent damage to containers, insulated wires, cables, and the like, caused by animals, especially gnawing rodents.

2. Background Art

Rodents have long been known worldwide for their destructive habits and behaviors. They carry numerous diseases which infect humans, they eat or foul an astronomical quantity of food intended for people and domestic animals, and they cause an enormous amount of property damage as a result of their gnawing and burrowing.

Rodents appear to be genetically compelled to gnaw, and gnawing may be independent of factors such as food or water deprivation or satiation. For example, rodents (rats, mice, gophers, prairie dogs, etc.) gnaw at the rubber or plastic insulation of electric cables, eventually exposing the conductive wires and eventually causing a short circuit. Replacement or repair of gnawed cables can be time consuming and costly, especially when the damaged cables are overhead, buried in the ground, or within building walls. Gnawing-induced damage to fiber optic cables is particularly troublesome, since there is no voltage leak to facilitate detection and location of the damage. The growing use of fiber optic cables, together with the difficulty in locating, splicing and repairing these cables, increases the need for an effective means of protecting them from animal damage.

Numerous scientific laboratories, as well as a variety of public and private businesses and industries, experience serious problems with rodent damage to electric and fiber optic cables. Typically, expensive rodent-proof coverings (often called gopher-proofing), using steel jacketing and/or other costly materials, have been used to reduce rodent damage. Such jackets have the marked disadvantages of significantly increased cost, added cable weight transported to the field, reduced flexibility (which hinders installation), and reduced effective length of spooled cable taken to the field (due to the increased cable diameter attributable to the jacketing).

Likewise, rodents often gnaw their way through various containers to access the contents. A particular problem is the gnawing of rodents through food containers, resulting in lost and contaminated food.

Hazardous waste management companies also experience rodent damage problems. Liquid hazardous wastes typically are temporarily held in lined lagoons prior to long-term storage, treatment, or disposal. Temporary storage lagoons are simply holes in the ground lined with plastic sheets. Rodents chew through the plastic liners, thereby releasing the waste into the ground and potentially leading to ground water contamination.

There have also been reports of severe problems with rats destroying wallpaper and walls as they gnawed their way to the wallpaper paste (apparently the paste is tasty and/or nutritive to the rodents). It was discovered that adding chile pepper to the paste prevents gnawing damage. (Logue, A. W., *The Psychology of Eating and Drinking*, W. H. Freeman and Company, 1986, p. 92).

Anecdotal reports also have described applications of cayenne chile pepper to bird feeders to prevent rodents (typically squirrels) from pilfering the birdfood. Chile pepper, mixed with petroleum jelly and spread on the pole supporting the feeder, prevents rodents from gaining access to the feeder.

U.S. Pat. No. 631,738 to Dowie, et al., entitled *Composition for Expelling Rats*, discloses a means of expelling rats and other vermin using chili pepper (of undisclosed species) and hellebore as active ingredients. A substance is sprinkled on the premises where rats are troublesome, and from its intense irritating and burning qualities effectually prevents the vermin from again invading the places where it has been used.

Other patents also disclose use of peppers to deter rodents or other animals. U.S. Pat. No. 4,097,607 to Larson, entitled *Deterrent Composition, Method of Using Same, and Article Coated Thereby*, discloses a deterrent with active ingredients including cinnamic aldehyde (the active ingredient in the spice cinnamon) in vehicles comprised of denatured ethyl alcohol, beeswax, lard or petrolatum. U.S. Pat. No. 4,455,304 to Yaralian, *Composition for Repelling Birds*, discloses a substance of "finely divided" cayenne pepper and garlic powder, inert mineral material (dolomite, talc) and water for use in repelling birds from plants, fruit and fields. U.S. Pat. No. 4,775,532 to Clayton, entitled *Animal Repellant Composition*, discloses the composition of an olfactory repellent consisting of such substances as di(n-heptyl, n-noyl) adipate, cinnamic aldehyde, methyl nonyl ketone, quinine, and mixtures thereof.

U.S. Pat. No. 4,795,637 to Harding, Jr., entitled *Rodent Repellent Powders*, discloses the use of pepper powder to discourage rodents. U.S. Pat. No. 4,965,070 to Messina, entitled *Deer Repellant Formulation*, discloses a deer repellent comprised of either "liquid hot sauce such as that sold under the trademark GOYA," as a gustatory repellent or "hot pepper powder" as an olfactory repellent. Both repellents are to be applied to the surface to be protected. U.S. Pat. No. 5,226,380 to Fischer, entitled *Marine Organism Repellent Covering for Protection of Underwater Objects and Method of Applying Same*, discloses the placement of cayenne pepper particles within an adhesive applied to underwater objects in order to repel barnacles and mussels.

Others have attempted using "liquid hot sauce," cayenne pepper, "finely divided pepper," "chili pepper", and "finely divided dried pepper" in order to repel animals. No previous attempts have been made to extract the active, heat-producing alkaloids (capsaicinoids) from peppers for direct use as animal repellents. Likewise, no previous use has been made of the habañero pepper (*Capsicum chinense*) which has the distinction of being the hottest pepper known. Indeed the habañero is hundreds of times hotter than the hottest of cayenne (*Capsicum annuum*) or tabasco peppers (*Capsicum frutescens*).

Current methods and techniques for animal damage control generally involve aggressive and lethal techniques such as poisons, trapping and glue boards. These methods are non-selective and can, therefore, harm non-targeted species. In the case of poisons, long-term residues can be problematic. Fencing and netting (as well as other exclusionary methods) can be effective, and they have the benefits of not harming the environment or non-targeted species; however, they can be cumbersome and expensive. With the current visibility of animal rights and environmental groups, new means of reducing animal damage while causing less harm to the environment or wildlife species will become increasingly important. Accordingly, a need remains for an animal repellent which complies with Environmental Protection Agency standards and regulations.

Several articles are critical of traditional methods of animal control such as trapping or poisoning, but do not suggest the use of capsaicinoid extract repellents as an alternative. Acord, B. R., "Animal Damage Control: Are We Prepared for the Next Century?" *The Probe*, Issue 111, June 1991, pp. 1–5, suggests that a new paradigm must be forged that has a win/win orientation mindful of animal welfarists or animal rightists and an emphasis on wildlife damage management rather than animal control. Fitzwater, W. D., "Bird Limes and Rate Glues—Sticky Situations." *Proceedings of the Tenth Vertebrate Pest Conference*, R. E. Marsh, Ed., University of California, Davis, 1982, pp. 17–20, indicates that there is widespread use of sticky materials such as "glueboards" to catch rats and mice. Their popularity has risen with the increasingly negative public attitude towards use of pesticide chemicals. The use of glueboards may be limited by temperature, moisture, dust, vapors, and the like. Problems include the entanglement of non-targeted species.

SUMMARY OF THE INVENTION
(DISCLOSURE OF THE INVENTION)

The invention relates to an animal repellent that effectively exploits the natural aversion that animals, especially and including rodents, have for the chemical compounds called capsaicinoids which occur naturally in chili pepper plants. Capsaicinoids, including the chemical capsaicin, are the irritant ingredients responsible for the "hot" quality of peppers. Habañero peppers are probably the hottest species of peppers.

The invention provides modes for making and using an animal repellent composition comprising capsaicinoid extract from pepper plants. Habañero peppers are the preferred species of pepper for use in the invention, due to their comparatively elevated capsaicinoid content; any species of pepper, however, may be used. The extract of the invention may be prepared by mixing powdered pepper fruit with a solvent, thereby releasing the active repellent ingredients from the cellulose walls of the pepper and causing the active ingredients to enter into a liquid solution. The solution is filtered to remove solids, and the resulting liquid solution comprises an extract usable in a variety of ways to treat objects to be protected. Various embodiments of the invention utilize differing solvents to accomplish the preparation of the extract, with hydrocarbon-based solvents preferred. A variety of pepper-to-solvent formula ratios are employed, with high ratios producing more potent extracts.

The invention comprises several modes of increasing the potency of the repellent extract, such as heating the pepper-solvent mixture and stirring the pepper-solvent mixture. Repeated episodes of stirring, separated by periods when the mixture is permitted to sit undisturbed, also comprise an aspect of the invention. Similarly, the extract repellent may be prepared by mixing a pepper powder with a solvent, optionally repeatedly stirring and/or heating the mixture, filtering the liquid extract, and then mixing the filtered liquid extract into a second mixture of pepper powder and solvent, followed by further stirring and filtering. Repeated use of extract into solvent-pepper mixes in such a manner generates "double-treated," or exceptionally effective repellent composition.

Because the capsaicinoid extract is chemically compatible, on a molecular level, with modern polymeric coating products, the extract finds efficacious use as a repellent additive in such coatings. The repellent extract may be mixed with polymers and then applied to objects to be protected, thereby providing the object with the physical protection of the coating as well as the repellent quality of the extract. Because the extract cross-links or bonds with the polymers of the coating, the repellent quality is particularly long-lived on the treated object.

A primary object of the present invention is the provision of an effective means for reducing or preventing animal damage.

A further object of this invention is the provision of effective means for deterring animal damage without harming targeted or non-targeted species.

Yet another object of this invention is the provision of effective means for deterring animal damage without doing short-term or long-term damage to the environment.

Yet another object of the invention is the provision of an effective means for deterring animal damage that readily and inexpensively complies with federal environmental laws, including the Federal Insecticide, Fungicide and Rodenticide Act.

Still another object of the invention is the provision of an effective, natural, organic means for reducing or preventing animal damage.

A further object of this invention is the provision of effective means for reducing or preventing animal damage that may be applied to or incorporated within the object to be protected.

A further object of the invention is the provision of effective means for reducing or preventing animal damage which is resistant to water, heat and ultraviolet radiation.

A further object of the invention is the provision of effective means for extracting capsaicinoids from the habañero chile pepper and for the incorporation of the extract into various substances (rubber, plastic, paint, glue, paper, etc.) to be protected or to be used as protection for other objects.

An advantage of the invention is its use in redundant or "sacrificial" layers or coatings upon objects to be protected.

Another advantage of the invention is its ready mixture with polymeric substances affording chemical, ultraviolet light and/or water resistance.

Yet another advantage of the invention is its ease of manufacture and relatively low cost.

Another advantage of the invention is that the target animal or animals to be deterred are not killed, and the capsaicin at the concentration necessary for an effective deterrent is environmentally safe. Humans and non-targeted animals are not permanently or seriously harmed if they come in contact with objects treated with the invention.

Still another advantage of the invention is its miscibility with various coatings and finishing substances and solvents.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED
EMBODIMENTS (BEST MODES FOR
CARRYING OUT THE INVENTION)

The invention is based upon the natural aversion most animals have for a group of alkaloids called capsaicinoids, alkaloid substances which occur naturally in the fruit of various chile pepper plants. The principal capsaicinoids found in most pepper plants are capsaicin, capsico, and capsacutin. There can be up to six different capsaicinoids in one pepper and different peppers have different concentrations of capsaicinoids. The production of capsaicinoids is a form of chemical defense against herbivores, and thus acts naturally as an animal repellant. Smith, R. L., *Ecology and Field Biology*, p. 562 (3d Ed. 1980). Capsaicinoids are the chemicals responsible for the "hot" sensation associated with peppers. Capsaicinoids generate a spicy flavor in the mouth and a mild to sharp burning or stinging feeling when applied to mucous membranes.

The present invention may find satisfactory utility in the repulsion of a variety of animal pests and vermin, including noxious scavengers such as coyotes, skunks, and the like. Capsaicinoids are also insect repellents, and the invention may find practical application for the repulsion of various types of wood-boring insects. Likewise, birds, e.g. woodpeckers can be repelled by the invention, as well as certain types of marine animals such as barnacles. Rodents, however, have an extremely sensitive taste capability and are able to detect (and thus avoid in the future due to aversion behavior) very low concentrations of capsaicinoids. One part in 100,000 of capsaicin ($C_{18}H_{27}NO_3$) can be detected by humans in taste threshold studies; rodents are much more sensitive. Capsaicinoid extract from habañero chile powder, or the powder itself, suitably applied in an appropriate vehicle, is inexpensive when compared to the cost of damage caused by rodents.

An important aspect of this invention is the use of natural capsaicinoids, preferably from the habañero pepper, as a treatment substance for application to, or inclusion within, objects or materials to be protected from animal damage. Since capsaicin can withstand a temperature of up to 68° C., and because it is nearly insoluble in water (*Merck Index*, 9th Ed., p. 224), the invention offers long-term effective suppression of rodent damage. Capsaicin's therapeutic category is listed as a counterirritant (*Merck Index*, 9th Ed., p. 224); it is not a poison, and thus is environmentally preferable.

Commercially available pure capsaicin is very expensive. The present invention presents an alternative to pure capsaicin, by presenting an inexpensive mode of extracting from pepper plants the capsaicinoids along with the pepper plants' essential oils. The essential oils bear the active repellent ingredients. The essential oils are dissolved in a solvent, and the solution is chemically compatible with many modern polymeric substances.

Capsicum is the formal term used to refer to the dried ripe fruit of the various species of chili peppers, especially *Capsicum annuum* and *Capsicum frutescens*. For purposes of this disclosure and claims, however, "capsicum" shall include fresh, as well as dried, fruit of any (or any mixture of) the aforementioned species, and shall also include the fruit of the habañero pepper, *Capsicum chinese*. In order to distinguish among the various capsicums, and to provide for comparative measurement of their "hotness," the Scoville Scale has been formulated. The Scoville Scale, set forth in Table 1, compares the relative "heat" attributable to varieties of capsicum.

TABLE 1

| Source | Units |
| --- | --- |
| Mild bell pepper | 0 |
| Paprika | 0–150 |
| Bell peppers | 100–600 |
| NuMex Big Jim | 500–1,000 |
| Jalapeños | 2,500–5,000 |
| Cayenne | 30,000–50,000 |
| Tabasco ® | 30,000–50,000 |
| Habañeros | 200,000–300,000 |
| Pure capsaicin | 16,000,000 |

The Scoville Scale, formulated nearly a century ago, is based on subjective criteria, but nevertheless illustrates the comparative intensities of pepper hotness. Modern gas chromotographic and mass spectrometric analytic techniques are more precise and reliable modes of comparing the relative capsaicin content of various peppers, but generally support the information set forth in the Scoville Scale.

The hotness of the various capsicums is directly attributable to their capsaicinoid content. The capsaicinoid molecules are linked to the resin molecules which naturally occur in the plant. For heat production, capsaicin appears to be the most important of the capsaicinoids. Capsaicin ($C_{18}H_{27}NO_3$) is a principal active ingredient of cayenne pepper. Cayenne pepper, quite hot to human taste, is approximately 30,000 to 50,000 units on the Scoville scale. This may be compared to habañero pepper, whose relative heat ranges from 200,000 to 300,000 Scoville Units. The habañero chile appears to be the "hottest" pepper in the world; research has shown it may contain approximately 0.013 g of capsaicin per gram of capsicum. Accordingly, the use of habañero chile pepper as the source of capsaicin extract offers advantages of efficacy and economy. Besides occurring naturally in peppers, capsaicin has also been synthesized.

Capsaicinoids may be used to repel animals by mixing finely ground or powdered capsicum (e.g. habañero) with any suitable vehicle, such as paint, silicone rubber, caulking, or the like. The treated vehicle is then applied to the object to be protected. Due to the elevated capsaicin content of habañero peppers, the protection thus afforded is greater than using powders of milder peppers, such as cayenne.

Capsicums contain natural resins, particularly the terpene capsanthin, which is the carotenoid responsible for the orange-red color associated with ripe chili peppers. (*Merck Index*, 10th Ed. p. 224; Streitwieser, A. and Heathcock, C. H., *Organic Chemistry*, p. 1149 (2d Ed. 1981). In original usage, the term "resin" had reference to the polymeric exudations of certain plants, especially after the exudate had hardened after prolonged exposure to air or burial in the ground. Examples of these naturally occurring resins are rosin, copol and damar. Certain other similarly hard and brittle natural polymers, such as lac, are often also referred to as resins. These natural resins have long been used as components of surface coating materials, perhaps the most noteworthy being varnishes. Since the rise of synthetic polymers as commercially important materials (plastics with physical properties somewhat similar to the natural resins), "resins" has come to be practically interchangeable with the term "polymer." Moreover, "resin" is also used to refer to certain liquid prepolymer products, such as unsaturated polyester and epoxy prepolymers—which may be cross-linked to hard, somewhat brittle thermoset polymers, which are also confusingly referred to as "resins." Nevertheless, naturally occurring terpene resins continue to be used as tackifying agents in rubbers, adhesives, and surface coating products. (Alger, Mark S. M., *Polymer Science Dictionary*, pp. 210, 278, 415, 470 (Elsevier Science Publishers, LTD, London, 1989)).

Certain oils, frequently called "essential oils," naturally occur within the cellulose cell wall of the capsicum fruit. See, Streitwieser, A. and Heathcock, C. H., *Organic Chemistry*, p. 1151 (2d Ed. 1981). The essential oils are comprised in part of terpene carbon chains, to which the capsaicinoids are linked. Each variety of capsicum has a certain percentage, by weight, of capsaicinoid-bearing terpene oils.

Even greater repellent advantages are realized when, in the preferred embodiment of the invention, the essential oils are extracted from the capsicum, and the extract applied directly to an object to be protected. Thus, the capsaicinoid-bearing essential oils, rather than whole capsicum, serves as the repellent agent.

The invention includes two fundamental modes of extracting the essential oils from the capsicum. Preferably, organic solvents (e.g., hydrocarbon derivatives or distillates) are used as solvents, to dissolve the oils out of the capsicum. Common lacquer thinners containing ketone and methyl benzene are effective solvents. The oils that separate from the cellulose usually have the color, odor, and taste associated with the capsicum. Alternatively, the essential oils can be distilled from the capsicum using water, or even using certain plant oils such as common vegetable oil or linseed oil, or the like.

Thinner compounds, such as common lacquer thinners, are usually solvents for the coating or sealing compounds in modern surface covering products. The solvents are expected to evaporate after the application of the product to the surface. Thinner solvents are also used as a carrier substance to add or introduce additional resins and polymers to coating product mixes. Petroleum distillates and hydrocarbon derivatives are most commonly used as thinners/solvents for polymeric treatment products, and thus are the preferred solvents for use in the present invention for the extraction of capsaicinoids from capsicum. Specific and alternative solvents that find satisfactory use in the invention include, but are not limited to, naphtha, petroleum ether, toluene, xylene, denatured methyl or ethyl or isopropyl alcohols, ketones, trichloroethanes (e.g., 1,1,1 trichloroethane) and turpentine. Solvents can be selected for maximum effectiveness in and compatibility with the various surface covering/sealing products.

Hereafter in this specification and in the claims, the term "habañero" means finely powdered habañero capsicum. "Extract" means a liquid solution in which capsaicinoid-bearing essential oils are present due to contact of a solvent with capsicum.

In one embodiment of the invention, a capsaicinoid extract is obtained by mixing powdered capsicum, preferably habañero, with a liquid solvent, causing essential oils to leave the cellulose matrix and enter into solution. For habañero, the preferred powder/solvent solution contains between approximately 16 to 400 g by weight of capsicum per 1000 ml of solvent. The capsicum-solvent mix may then be applied directly to objects to be protected, and the solvent allowed to evaporate. As a result of the application of the extract, capsaicinoids will remain upon the surface of the object, where its repellent quality remains active even in the event the capsicum solids sluff off. This mode of treatment is particularly useful for protecting containers, e.g., cardboard boxes, paper or cloth sacks, and the like, into which the capsaicinoids may be absorbed, adsorbed, or otherwise disposed, along with the extract. The solvent may be water, denatured alcohol, or petroleum distillates such as lacquer thinner, or other suitable solvent.

The foregoing embodiment of the invention may be used to protect wiring, cables, conduits, and the like. Strips of cardboard, paper, or other absorbent material are dipped or soaked in the capsicum-solvent mixture, and then wrapped around the wire, or otherwise applied to or disposed next to some other object to be protected. The solvent is free to evaporate, leaving the treated absorbent material to effectively repel the animals.

It may be desirable to cover an object to be protected with a layer of treated material that may be "sacrificed," e.g. chewed or gnawed. In this manner, the animals acquire an aversion to the capsaicinoids before gaining access to the protected object.

In a preferred embodiment of the invention, capsicum, preferably habañero, is mixed with at least one liquid solvent to obtain a capsicum-solvent mix. For habañero, the preferred capsicum-solvent mix contains between approximately 16 g to 400 g by weight of capsicum per 1000 ml of solvent(s). The mixture then is filtered to separate the capsaicinoid-containing liquid solution from the capsicum cellulose solids. The filtered liquid extract is then used to treat any of a variety of application vehicles which are then applied to the object to be protected. Treatment of application vehicles is accomplished by mixing the extract with the application vehicle prior to applying the application vehicle to the surface to be protected. Filtering the mix separates the pepper solids from the liquid extract, thus allowing the extract to be mixed with an application vehicle while avoiding the introduction into the vehicle of solid contaminants.

After the capsicum solids are removed, the resultant capsaicinoid-bearing extract shares the properties of the solvent(s) and the essential oils. In this liquid phase the essential oils, comprising natural polymers, can advantageously be introduced into liquid plastics, silicones, paints, polyurethanes and other polymer products (natural or synthetic). Because the essential oils are comprised mostly of terpene resins, the essential oils are chemically very compatible with modern artificial polymeric surface coating products. Accordingly, the invention offers a mode of incorporating the active repellent ingredient directly into the polymer matrix of modern coating and adhesive compositions. The precise solvent used to extract the essential oils from the capsicum is also preselected to be compatible with whatever polymer application vehicle is desired.

"Application vehicles" are substances used to coat, cover, or seal objects. Suitable application vehicles include, but are not limited to, paints (enamel, alkyd), caulks, rubbers (including both natural and synthetic rubbers, such as silicone), liquid plastics, vinyls, epoxies, acrylic resins, wood enamels and wood preservatives (polyurethane). Certain plant oils, such as linseed oil, can dually serve as solvents and as application vehicles.

When in solution with organic solvents, the essential oils are homogeneously dispersed, and there is no evident separation of molecular components. When the extract is mixed into polymeric vehicle, such as a clear liquid silicone, there also appears to be a homogeneous dispersion of the extract throughout the vehicle.

Thus, when a vehicle is treated with the extract and then applied to a surface and allowed to cure, the resultant protective coating has the advantageous animal repellent properties of the extract as well as the desirable physical characteristics (e.g., water-proofness) of the vehicle.

Thus, the extract may be mixed with oil (or, alternatively, water-based) substances to provide protection for painted or coated surfaces. The powder or extract also may be incorporated directly into rubbers, glues or plastic materials, which may then be applied to or form a part of the insulation layer of wires, cables, conduits, and the like. Such materials may also coat or be incorporated into trash bags, foam rubber, wood, cloth, paper or cardboard to form a barrier against rodents. In all examples, the selection of a particular solvent or carrier will depend upon the compatibility of the particular vehicle into which it is to be incorporated, mixed or applied.

In alternative embodiments of the invention, exceptionally "hot" capsaicin extract repellents may be derived by mixing capsicum and solvent, filtering out the liquid extract, and then mixing the filtered extract with more pepper and solvent, the new mixture also being filtered to obtain a "double-treated" extract.

The invention includes the use of methodologies for increasing the concentration of capsaicinoids in the extract. Stirring the capsicum-solution mixture also promotes extraction of essential oils from the capsicum. An aspect of the invention is the determination that the mixture should be stirred at least once, and that the episodes of stirring typically should last from at least fifteen seconds up to about three minutes, after which further stirring does not sufficiently increase potency to justify the additional processing time. Preferably, high-speed stirring or blending of the capsicum with the solvent is performed in an industrial grade blender. (Conventional laboratory/household blenders commonly cannot withstand the potent organic solvents featured in the invention.) A stirring time of 15–30 minutes is preferred. Longer periods of mixing produce more potent repellent, but stirring times longer than 30 minutes are not usually justified by sufficiently increased potency.

Additionally, the concentration of the capsaicin in the extract may be increased, generating a "hotter" extract, by allowing the mixture to sit undisturbed between episodes of stirring. The number and length of the periods of time the mixture is allowed to sit may be increased to increase the intensity of the repellent quality. In most embodiments of the invention, one or more "rest" or "sitting" times during which the mixture is allowed to set have a duration of at least fifteen seconds in order to promote the solution of capsaicinoid-bearing essential oils. Allowing the mixture to set for over two minutes generally is not time-efficient, although an embodiment of the invention includes the step of allowing the mixture to set for a full day.

The capsicum-solvent mixture may be heated, preferably to a temperature range of between approximately 60° C. and 75° C., while it is stirred to promote the molecular interaction fostering solution of capsaicinoids into the solvent.

Pulverizing the capsicum to extremely fine powder generally increases the potency of the extract. Very fine powders contribute to the efficacy of the repellent, and may also reduce stirring times or reduce solvent requirements.

In all embodiments of the invention, the relative quantities of capsicum and solution are established to adjust the potency of the repellent. The greater the ratio of capsicum (weight) to solution volume, the hotter the resultant extract. The capsicum, however, may be the most expensive ingredient of the capsicum/solvent mix, and the invention, therefore, consists in part of a determination of the minimum quantity of pepper required, per volume of solvent, to obtain an efficacious repellant extract. Petroleum distillates are a more effective solvent than water, and increasing the efficacy of the solvent employed produces a concomitant increase in the potency of the repellent extract.

An important advantage of the invention is, therefore, the chemical compatibility of the terpene resins (comprised of unsaturated carbon chains) of the essential oils with the polymers of commercially available natural and synthetic surface coating products. Substantial cross-bonding may occur between the capsaicinoids of the inventive extract and the polymers of various application vehicles. The solvents, such as lacquer thinner, used in the invention are compatible with a wide variety of common polymer products as well as serving as the carrier for capsaicin-bearing extracts to be mixed into such products. Certainly, the addition of repellent extract according to the invention into manufactured surface coating/sealing products can be accomplished at the point and time of manufacture.

The present invention is a substantial improvement upon the simple notions of sprinkling ground capsicum around an area to be protected, or merely mixing ground capsicum into glues or paints. The present invention, by providing for the extraction of the capsaicinoid-bearing essential oils, allows the direct use of the active, repellent, chemical agent. The user of the invention can apply the active repellent extract directly onto the item to be protected. Even more advantageously, the chemical compatibility between polymer coating products and the repellent extract can be exploited to provide treated coating vehicles that offer advantages of both surface protection from physical and weather damage as well as protection from animal damage.

The invention is further described by the following non-limiting examples.

CAPSAICINOID EXTRACTIONS

A number of demonstrations of various aspects of the invention were performed. The petroleum solvent frequently used to obtain extract was lacquer thinner. Lacquer thinners having the following ingredients were used essentially interchangeably (although precise solvent formulae may be customized to be compatible with particular application vehicles, if desired):

| Solvent A | Solvent B |
|---|---|
| Isobutyl isobutrate | Methyl ethyl ketone |
| Methyl ethyl ketone | Toluene |
| Methyl isobutyl ketone | Aliphatic petroleum |
| Methyl alcohol | distillate |
| Lactal spirits | Ethylene glycol |
| Toluene | Monobutyl ether |
| | Methyl alcohol |

| Solvent C |
|---|
| Methyl ethyl ketone |
| Naphtha |
| Toluene |
| Hexane |

EXAMPLE 1

Five hundred ml (500 ml) of lacquer thinner was mixed with 200 ml denatured alcohol and 112 g of habañero. The mixture was heated in a water bath at 75° C. for 2 h. The mixture was then cooled and passed through filter paper to separate particulate solids from the liquid extract.

The resultant liquid extract can be painted, sprayed, or applied in any suitable manner to objects in order to protect those objects from rodent damage. Addition of the extract to other protective coatings, for example PLASTI DIP®, provided enhanced resistance to chemical, ultraviolet light, and water damage. PLASTI DIP® is a trademark of PDI, Inc., Post Office Box 130, Circle Pines, Minn. 55014, for its plastic coating product, U.S. Pat. No. 1,536,151.

EXAMPLE 2

One thousand ml (1000 ml) denatured alcohol was mixed with 200 g habañero. The mixture was blended at high speed for 10 minutes, then poured through filter paper to separate solid constituents from liquid. The collected liquid filtered extract is especially efficacious as a spray or dipping bath for paper, cardboard, and similar products.

EXAMPLE 3

One hundred g (100 g) vegetable oil was mixed with 50 g habañero. The mixture was then combined with 305 g of rubber (latex) coating (as used for making casts). The resulting mixture may be painted or otherwise applied to the object to be protected and allowed to dry. Thus applied, the mixture provided a durable protective coat.

EXAMPLE 4

One hundred g (100 g) of extract, as prepared in Example 1 was combined with 200 g of silicone sealant. The resulting mixture is used as a caulk, sealant, or coating.

EXAMPLE 5

Finely powdered habañero, 100 g, was combined with 200 ml lacquer thinner at a temperature of 75° F. The mixture was stirred vigorously for two minutes and allowed to set for one minute; then stirred for another two minutes and allowed to set for two more minutes.

Habañero, 100 g, was added to the above powder-thinner mixture and 200 ml of lacquer thinner. The resulting mixture was stirred for two minutes, allowed to set for one minute, then stirred for another two minutes and again allowed to set for two minutes (all at 75° F.). The mixture was filtered through filter paper, and the liquid was collected and retained. The separated liquid was allowed to set for 10 minutes. The mixture was then again stirred for two minutes, and allowed to set for one minute, stirred for another two minutes and then allowed to set for two minutes (again, all at 75° F.). The liquid extract was stored for 24 hours (and allowed to cool to room temperature), then gravity filtered through filter paper to remove solid particulates from liquid extract, and the latter was again collected and retained. The yield was approximately 350 ml of a concentrated, very hot extract.

The concentrated extract may be used with an air dry synthetic rubber coating substance, e.g., PLASTI DIP®. To use with a synthetic rubber coating substance, 269 g of synthetic rubber was mixed with 175 ml of the concentrated extract and stirred until thoroughly mixed. The resultant rubber/extract mixture can is useful as a repellent paint or dip.

EXAMPLE 6

In a 1000 ml glass jar, 800 ml of lacquer thinner (or other suitable solvent) was added to 112 g of finely powdered habañero. A loose-fitting lid was applied. The glass jar was placed in a 60° C. water bath and stirred continuously for 8 hours. After 8 hours of stirring, the mixture was cooled to 75° F. The mixture was allowed to pass by gravity through filter paper to remove solid constituents. The treated solution was retained. The yield was approximately 500 ml of extract (due to liquid losses attributable to evaporation during heating and stirring and to absorption into the habañero).

The extract thus prepared may be used with silicone rubber sealants such as GE Silicone II® Window and Door Sealant, Stock #GE 500, or DOW CORNING® 100% Silicone Sealant, Reorder Cat. No. 8646. To use with a silicone rubber sealant, 200 ml of the extract thus prepared was added to approximately 300 ml of silicone sealant, and mixed thoroughly. (It will be appreciated that combination of extract with sealant may ideally be accomplished at the point and time of sealant manufacture, prior to packaging, in commercial production of the invention.)

To use the extract with an air dry synthetic rubber coating, e.g., PLASTI DIP®, 200 ml of extract was added to 300 ml of synthetic rubber coating and mixed thoroughly. The resulting treated mixture may be used immediately or stored for two or three days.

EFFICACY STUDIES

Following are several comparative examples of rodent damage to objects protected or unprotected by the invention. In all the example tests, a "small subject, repeated measures" study design was utilized, whereby a small sample number of animals was used, with individual animals undergoing more than one test.

Long-Evans hooded rats (both sexes, adults) are capable of removing all the insulation from a 10-inch piece of stranded 6-gauge electrical wire in less than two hours. Approximately 90% to 95% of the insulation is simply stripped off and dropped to the cage floor. The remaining insulation appears actually to be ingested by the animal, as it can be recovered in the feces. In addition to stripping away the insulation, the rodents can damage the conductive wires with small nicks or deep bite marks. In 24-hour tests, the majority of the wire damage occurs during the dark phase of the lighting cycle, and significant damage can occur in less than one hour (more than 2-inches of insulation removed from a 10-inch piece of wire). Onset and duration of gnawing on cables appears to be unaffected and independent of food or water deprivation or satiation.

EXAMPLE 7

Six naive adult Long-Evans hooded rats (three of each sex) were removed from their individual suspended wire mesh cages (20.5 cm W×18 cm H×24.5 cm D) in the breeding colony room, transported to an empty lab and placed into individual plastic cages (opaque polycarbonate, 6.25 inches high×12 inches wide×14 inches deep) with stainless steel wire bar lids. The cage floors were covered with approximately one inch of sterilized hard wood chips (Sani-Chips™). Food (Harlan® Teklad Laboratory Rodent Diet) and fresh tap water were freely available at all times. The animals remained in the plastic cages and lab throughout the course of the test. Overhead fluorescent strip lighting was cycled on at 7 a.m. and off at 7 p.m. Lab temperature was thermostatically maintained at 26° C. ±2° with humidity set at 45%.

Treated (protected with extract of habañero) and non-treated wires were prepared for the tests. All test wires were prepared from identical 10-inch long, 6-gauge, multi-stranded copper conductor cable. Treated wires consisted of six dipped coats (with ample drying time between coats) of PLASTI DIP® containing habañero extract repellent, prepared as per Example 1 above. The six coats resulted in a total thickness of approximately 1.0 mm. Control wires were coated with six dips of untreated PLASTI DIP®. A within-subjects, repeated measures experimental design was used. A non-treated control wire placed on the cage floor awaited each animal as it was placed into its plastic cage. The wire was then allowed to remain in the cage for 72 hours.

At the end of 72 hours, the wires were removed and the damage was noted. Approximately 90% of the insulation was removed from the wires with significant amounts of damage to the copper conductor. The control wires were then replaced with treated wires and allowed to remain in the cages for 72 hours. At the end of this period the wires were removed and the damage was assessed. No evidence of any damage was observed. Fresh (i.e., not previously exposed to animals) untreated wires were again placed in each cage for another 72 hours. At the end of this period, the wires were removed and again the damage was noted. Damage was extensive with approximately 90% of the insulation removed with additional damage to the copper conductors. Fresh treated wires were then placed in the cages for two weeks. Again, no evidence of any damage was observed. Finally, fresh untreated wires were put in the cages with significant and virtually identical damage as before following 72 hours of access.

SUMMARY OF EXPERIMENTAL DESIGN AND RESULTS

Access to control wires for 72 hours followed by damage assessment≈90% stripped of insulation Access to treated wires for 72 hours followed by damage assessment=No damage Access to control wire for 72 hours followed by damage assessment≈90% stripped of insulation Access to treated wires for 14 days followed by damage assessment=No damage Access to control wires for 72 hours followed by damage assessment≈90% stripped of insulation

EXAMPLE 8

Ten naive hooded rats (five of each sex) were housed and fed as in Example 7. The same experimental design as in Example 7 was also used, except that animals were allowed to habituate in the plastic cages for 14 days prior to the first wire test. Wire was also the same except for the coating. In this example, the protected wire was coated with a mixture consisting of habañero powder added to General Electric silicone caulk/sealant. The control wires were treated with the silicone caulk/sealant without the protective habañero additive. The coating in the treated and untreated wires produced a layer approximately 2 mm thick. Fresh wires, not previously exposed to animals, were used in each phase of the test.

SUMMARY OF EXPERIMENTAL DESIGN AND RESULTS

After habituation to plastic cages for 14 days:

Access to control wires for 24 hours followed by damage assessment=100% stripped of insulation Access to treated wires for 72 hours followed by damage assessment=No damage Access to control wires for 24 hours followed by damage assessment=100% stripped of insulation Access to treated wires for 8 days followed by damage assessment=No damage Access to control wires for 24 hours followed by damage assessment=100% stripped of insulation Access to treated wires for 30 days followed by damage assessment=No damage Access to control wires for 24 hours followed by damage assessment=100% stripped of insulation

EXAMPLE 9

Fifteen naive hooded rats were fed and watered as in Examples 7 and 8, and housed in groups of three to a cage (two female, one male). The wire to be protected was dipped six times into a mixture consisting of 175 ml of extract prepared as per Example 1 added to 429 ml of PLASTI DIP®. Control wires were identically dipped into treated PLASTI DIP®. After thorough drying, both treated and control wires were subjected to individual 20° C. water baths (1 gal/min) for seven days prior to being placed in the animals' cages. Fresh wires were used in each phase of the testing.

SUMMARY OF EXPERIMENTAL DESIGN AND RESULTS

The animals were habituated to plastic cages for 14 days.

Access to control wires for 72 hours=All wires in all groups 100% stripped of insulation Access to treated wires for 72 hours=No damage Access to control wires for 12 hours=All wires in all groups 100% stripped of insulation Access to treated wires for 72 hours=No damage Access to control wires for 12 hours=All wires in all groups 100% stripped of insulation Access to treated wires for 72 hours=No damage Access to control wires for 12 hours=All wires in all groups 100% stripped of insulation The foregoing results show that the mixture of the repellent extract of the invention with waterproof application vehicles, such as synthetic rubbers, produces a repellent coating that can withstand substantial exposure to rinsing conditions without suffering a noteworthy loss in repellent efficacy.

EXAMPLE 10

Three rats (1 male, 2 female, Long-Evans hooded, adult, naive, were individually caged. Recycled cardboard was treated as follows. Ten grams (10 g) of habañero was added to 300 ml of distilled water. The mixture was blended for 10 min. at high speed. Cardboard test strips (4 cm×10 cm and approximately 1 mm thick) were soaked for 30 seconds in the mixture. After air drying, the treated cardboard was wrapped around 9-cm, 4 gauge, multistranded, insulated copper wire. The cardboard was secured using electrical tape at each end. Each animal was exposed to each condition (i.e., unwrapped, wrapped with untreated cardboard, and wrapped with treated cardboard) for 24 hours, and a new wire was used for each 24 hour test.

| Summary of Experimental Design and Results: |||
| --- | --- | --- |
| Wire conditions | Time in cage | Results: wire damage |
| Unwrapped | 48 hrs. | At least 75% stripped |
| Wrapped-untreated cardboard | 48 hrs. | At least 75% stripped |
| Wrapped-treated cardboard | 120 hrs. | No damage to cardboard or wire |

In all instances of control conditions for all animals, the cables were damaged to the point of exposing bare wires. In all instances of treated conditions, the cardboard showed little or no damage. The wire's insulation layer was not damaged.

EXAMPLE 11

Twelve rats (6 of each sex, Long-Evans hooded, adult, naive) were individually caged.

Recycled cardboard was treated with three different concentrations of extract as follows. The three concentrations of extract were prepared by adding 5, 10 or 15 g, respectively, of habañero to 300 ml of distilled water. Mixtures were blended for 10 minutes at high speed. Cardboard test strips (4 cm×10 cm and approximately 1 mm thick) were soaked in each mixture. The treated cardboard was air dried and then wrapped around 9-cm, #4 gauge, multistranded, insulated copper wire. The cardboard wrapping was secured using electrical tape at each end. The animals were exposed to unwrapped wire, wire wrapped with untreated cardboard, and wire wrapped with treated cardboard.

Experimental design: Small subject with repeated measures.

| Summary of Experimental Design and Results: |||
| --- | --- | --- |
| Wire conditions | Time in cage | Results: wire damage |
| Unwrapped | 48 hrs | At least 75% stripped |
| Wrapped-untreated cardboard | 48 hrs | At least 75% stripped |
| Wrapped-treated cardboard (5 g) | 120 hrs | No damage to cardboard or wire |
| Wrapped-treated cardboard (10 g) | 120 hrs | No damage to cardboard or wire |
| Wrapped-treated cardboard (15 g) | 120 hrs | No damage to cardboard or wire |

EXAMPLE 12

Eight rats (4 of each sex, Long-Evans hooded, adult, naive) were individually caged. Males averaged 480 g in weight, females 265 g.

Treated cardboard test strips were prepared as follows: 105 g of habañero was added to 1000 ml of tap water, and the mixture blended at high speed for 10 minutes. Cardboard test strips (4 cm×10 cm and approximately 1 mm thick) were soaked in the blended mixture. The treated cardboard strips were air dried and then wrapped around 9-cm, #4 gauge, multistranded, insulated copper wire. The cardboard was secured around the wire using electrical tape at each end. Fresh cardboard/wires were used for each of three phases of the experiment. The animals were exposed to wires wrapped with treated cardboard and wires wrapped with untreated cardboard.

| Summary of Experimental Design and Results: Experimental design: Small subject, repeated measures. |||
| --- | --- | --- |
| Cardboard conditions | Time in cage | Results: wire damage |
| Untreated I | 72 hours | Severe to cardboard (75% stripped) and wire |
| Treated I | 72 hours | None |
| Untreated II | 72 hours | Severe to cardboard (75% stripped) and wire |
| Treated II | 72 hours | None |
| Untreated III | 72 hours | Severe to cardboard (75% stripped) and wire |
| Treated III | 11 days | None |

In conjunction with this test, the wire and cardboard samples were weighed before and after exposure to the animals. Raw data showing the changes in weight attributable to gnawing damage to the wire corresponding to each animal are set forth in Table 2. Absolutely bare wires, stripped of all covering, ranged in weight between 5.3 and 5.7 grams.

TABLE 2

| | (Weight of wires in grams) ||||
| --- | --- | --- | --- | --- |
| | Untreated I || Treated I ||
| | Before | After 72 hrs | Before | After 72 hrs |
| 1 | 16.01 | 5.37 | 16.92 | 11.16 |
| 2 | 16.07 | 6.70 | 16.91 | 13.98 |
| 3 | 16.03 | 8.49 | 16.70 | 16.86 |
| 4 | 16.04 | 6.33 | 16.79 | 16.95 |
| 5 | 16.04 | 5.67 | 17.01 | 13.01 |
| 6 | 16.05 | 5.66 | 16.91 | 11.38 |
| 7 | 16.04 | 6.10 | 16.71 | 16.66 |
| 8 | 16.02 | 6.76 | 16.57 | 16.33 |
| | Untreated II || Treated II ||
| | Before | After 72 hrs | Before | After 72 hrs |
| 1 | 16.03 | 5.31 | 16.76 | 15.12 |
| 2 | 16.04 | 12.53 | 16.57 | 16.66 |
| 3 | 16.05 | 8.54 | 16.69 | 16.73 |
| 4 | 16.02 | 6.20 | 16.67 | 16.75 |
| 5 | 16.06 | 6.95 | 16.66 | 16.06 |
| 6 | 16.10 | 5.33 | 16.76 | 6.84 |
| 7 | 16.08 | 7.55 | 16.67 | 17.41 |
| 8 | 16.02 | 12.56 | 16.66 | 15.80 |
| | Untreated III || Treated III ||
| | Before | After 72 hrs | Before | After 72 hrs |
| 1 | 15.65 | 5.37 | 16.77 | 16.76 |
| 2 | 15.44 | 5.80 | 16.59 | 16.72 |
| 3 | 15.74 | 8.50 | 16.43 | 16.44 |
| 4 | 15.37 | 6.14 | 16.50 | 16.56 |
| 5 | 15.69 | 5.33 | 16.62 | 16.72 |
| 6 | 15.76 | 5.35 | 16.60 | 12.11 |
| 7 | 15.77 | 6.02 | 16.71 | 16.85 |
| 8 | 15.81 | 6.00 | 16.46 | 16.41 |

In all phases of this Example 12, untreated wires suffered extensive damage, up to and including complete stripping of all insulation and cardboard. In the Untreated I phase of this Example, subjects 1,5 and 6 resulted in all the cardboard being shredded and the insulation stripped, leaving the conductive wires bare. Subjects 2,3,4,7 and 8 of Untreated I phase resulted in nearly completely bare wire, with minor amounts of residual cardboard remaining intact. Untreated II and Untreated III phases of the test produced similar results;

reference to Table 2 indicates that all unprotected wires suffered substantial weight loss (completely bare conductive wires weighing between 5.3 and 5.7 grams inclusive) due to complete or nearly complete stripping of insulation and cardboard. Subjects 2 and 8 of the Untreated II phase of the test were somewhat aberrational, in that once the animals had penetrated a portion of the cardboard to expose the underlying wire, further gnawing effort was directed mostly to the exposed wire rather than the remaining unstripped cardboard.

EXAMPLE 13

Six rats (3 of each sex, Long-Evans hooded, adult, naive) were individually caged. The males averaged 414 g in weight, females averaged 271 g. Both sexes were three months old. The test was videotaped.

Wires used in the test were 14 cm long, 10 gauge, multistranded with rubber insulation. Prior to coating, the wires averaged 7.10 g in weight. After being covered with a treated coating, the wires had an average weight of 8.48 g. The average weight of a wire completely stripped of insulation wire was 6.30 g. Treated wires had coatings approximately 1 mm thick (six coats).

The treated coating substance was prepared using a two-mixture method. To obtain an extract using lacquer thinner as a solvent, 400 gm habañero was mixed with 1000 ml lacquer thinner. The mixture was hand mixed for 2 minutes at the rate of two stirs per second, and was then allowed to set for 1 minute, and was then further mixed for 2 minutes at two stirs per second. The mixture was then filtered through filter paper to separate the liquid extract. The liquid extract was collected in a container for later use. (This extract was suitable for use as a repellent without further processing, but in the test was further mixed with additional capsicum and solvent, as described below.)

Next, 200 gm of habañero was combined with 400 ml of lacquer thinner. The mixture was blended at high speed for 2 minutes, then allowed to set for 1 minute, and then again blended for 2 minutes. The twice-blended mixture was then filtered through filter paper to obtain the liquid extract, and the extract collected and retained. In a separate container, 200 g of habañero was mixed with 450 ml of lacquer thinner. To this mixture was added 150 ml of the filtered liquid extract solution as prepared above, and the three ingredients were then thoroughly mixed. This method produced a somewhat "hotter" extract using lacquer thinner as solvent.

A treated synthetic rubber was fashioned using the substance prepared according to the above-described method. Into one container of PLASTI DIP® (14.5 fluid oz.), 175 ml of treated solvent, prepared according to the immediately above-described method was added. Incorporation of the treated solvent prepared according to the alternative method resulted in the formulation of a hotter synthetic rubber.

Wires protected according to the invention were dipped into the treated PLASTI DIP® (e.g. PLASTI DIP®-extract mixture) a total of six times, producing a layered coating approximately 1 mm thick. Control wires were dipped six times in untreated PLASTI DIP®. Fresh wires were employed for each phase of the test.

Summary of Experimental Design and Results:
Experimental design: Small subject, repeated measures.

| Condition | Time in cage | Results |
|---|---|---|
| Control wire I | 72 hours | Severe wire damage |
| Treated wire I | 72 hours | No wire damage |
| Control wire II | 72 hours | Severe wire damage |
| Treated wire II | 14 days | No wire damage |
| Control wire III | 72 hours | Severe wire damage |

Both the treated test wires and the untreated control wires were weighed before and after their exposure to the animals, generating the data found in Table 3 for the wire corresponding to each of the six animals.

TABLE 3

(weight of wires in grams)

| | Untreated I | | Treated I | |
|---|---|---|---|---|
| | Before | After 72 hrs | Before | After 72 hrs |
| 1 | 8.50 | 6.85 | 8.39 | 8.39 |
| 2 | 8.52 | 7.87 | 8.35 | 8.35 |
| 3 | 8.46 | 7.19 | 8.45 | 8.11 |
| 4 | 8.51 | 6.65 | 8.46 | 8.46 |
| 5 | 8.67 | 7.44 | 8.40 | 8.40 |
| 6 | 8.48 | 6.35 | 8.45 | 8.45 |

Untreated wires were totally stripped of insulation

| | Untreated II | | Treated II | |
|---|---|---|---|---|
| | Before | After | Before | After 14 days |
| 1 | 8.49 | 7.83 | 8.45 | 8.45 |
| 2 | 8.58 | 8.30 | 8.36 | 8.36 |
| 3 | 8.45 | 7.31 | 8.48 | 8.45 |
| 4 | 8.53 | 8.31 | 8.43 | 8.44 |
| 5 | 8.64 | 7.30 | 8.36 | 8.36 |
| 6 | 8.43 | 6.20 | 8.36 | 8.39 |

Untreated wires were totally stripped of insulation

| | Untreated III | |
|---|---|---|
| | Before | After 72 hrs |
| 1 | 8.51 | 6.98 |
| 2 | 8.48 | 7.90 |
| 3 | 8.59 | 7.55 |
| 4 | 8.45 | 8.25 |
| 5 | 8.49 | 7.20 |
| 6 | 8.55 | 6.31 |

Untreated wires were totally stripped of insulation

In this Example 13, some variability in the weights, after animal exposure, of the three Untreated phases of the test is attributable to minor amounts of insulation that were rendered inaccessible to the animals due to the mode of securing the sample wires within the cages.

EXAMPLE 14

10 rats (5 male, 5 female, Long-Evans hooded, adult, naive) were individually caged. The males averaged 502 g and the females averaged 305 g in weight. Both sexes were three months old. The test was video taped.

One 10-gauge, multistranded copper wire, 10 inches long was placed in each animal's cage. To approximately 300 ml of silicone sealant. 200 ml of extract (prepared as per Example 6) was added and thoroughly mixed. New wires (control or treated) were used for each phase of the test.

Summary of Experimental Design and Results:
Experimental design: Small subject, repeated measures.

| Condition | Time in cage | Results |
|---|---|---|
| Control wire I | 24 hours | Wires completely stripped |
| Treated wire I | 72 hours | No damage |
| Control wire II | 24 hours | Wires completely stripped |
| Treated wire II | 8 days | No damage |
| Control wire III | 24 hours | Wires completely stripped |
| Treated wire III | 30 days | No damage |
| Control wire IV | 12 hours | Wires completely stripped |

Both the treated test wires and the untreated control wires were weighed before and after their exposure to the animals, generating the data found in Table 4 for the wire corresponding to each of the ten animals.

TABLE 4

(wire weights in grams)

| | Untreated I | | Treated I | |
|---|---|---|---|---|
| | Before | After 72 hrs | Before | After 72 hrs |
| 1 | 5.08 | 2.30 | 4.34 | 4.30 |
| 2 | 4.91 | 2.13 | 4.74 | 4.70 |
| 3 | 4.77 | 2.32 | 4.46 | 4.38 |
| 4 | 4.98 | 2.07 | 4.57 | 4.51 |
| 5 | 4.92 | 2.03 | 4.61 | 4.55 |
| 6 | 4.88 | 1.96 | 4.74 | 4.63 |
| 7 | 4.92 | 2!!.40 | 4.45 | 4.32 |
| 8 | 4.83 | 1.97 | 4.75 | 4.70 |
| 9 | 4.92 | 1.87 | 4.60 | 4.55 |
| 10 | 4.73 | 2.03 | 4.64 | 4.59 |

Untreated wires were totally stripped of insulation

| | Untreated II | | Treated II | |
|---|---|---|---|---|
| | Before | After 12 hrs | Before | After 8 days |
| 1 | 4.42 | 4.12 | 4.87 | 4.88 |
| 2 | 4.53 | 2.45 | 4.88 | 4.74 |
| 3 | 4.30 | 2.48 | 4.95 | 4.93 |
| 4 | 4.41 | 1.99 | 4.74 | 4.36 |
| 5 | 4.40 | 2.53 | 4.67 | 4.64 |
| 6 | 4.66 | 2.29 | 4.56 | 4.55 |
| 7 | 4.54 | 2.51 | 4.62 | 4.64 |
| 8 | 4.70 | 2.02 | 4.76 | 4.77 |
| 9 | 4.62 | 2.47 | 4.73 | 4.73 |
| 10 | 4.63 | 1.99 | 4.76 | 4.73 |

Untreated wires were totally stripped of insulation

| | Untreated III | | Treated III | |
|---|---|---|---|---|
| | Before | After 12 hrs | Before | After 30 days |
| 1 | 4.16 | 4.16 | 3.81 | 3.84 |
| 2 | 4.12 | 1.99 | 3.89 | 3.88 |
| 3 | 4.08 | 1.97 | 4.28 | 4.26 |
| 4 | 4.17 | 2.05 | 4.15 | 4.15 |
| 5 | 4.11 | 2.04 | 4.27 | 4.27 |
| 6 | 3.99 | 1.96 | 4.10 | 4.10 |
| 7 | 4.11 | 1.98 | 4.07 | 4.16 |
| 8 | 4.13 | 1.99 | 4.15 | 4.22 |
| 9 | 4.06 | 2.00 | 4.09 | 4.09 |
| 10 | 4.10 | 2.04 | 4.11 | 4.21 |

Untreated wires were totally stripped of insulation

| | Untreated IV | |
|---|---|---|
| | Before | After 12 hrs |
| 1 | 3.98 | 2.06 |
| 2 | 4.12 | 2.05 |
| 3 | 3.81 | 2.02 |
| 4 | 4.25 | 2.03 |
| 5 | 4.13 | 2.02 |
| 6 | 4.13 | 2.03 |
| 7 | 3.94 | 2.00 |
| 8 | 4.05 | 2.04 |
| 9 | 3.96 | 2.03 |
| 10 | 3.55 | 2.06 |

Untreated wires were totally stripped of insulation

EXAMPLE 15

Five rats (3 females, 2 males, Long-Evans hooded, adult, naive) were individually caged. Males averaged 321 g in weight, females averaged 210 g, and both sexes were two months old.

The treated coating of the test was prepared according to the following method: (1) To 500 ml of solvent (lacquer thinner) was added 200 grams of habañero powder. The mixture was hand mixed for 2 minutes at 2 stirs per second, allowed to set for 1 minute, and then again mixed for 2 minutes. The mixture was then allowed to set for 24 hours at 70° F. After 24 hours, the mixture was hand mixed as before and then filtered to separate the liquid extract. (2) 200 g of habañero was added to 400 ml of solvent (lacquer thinner). The combination was hand mixed as in Step 1. 290 ml of the treated solvent in Step 1 was added to the mixture, and the mixture was hand mixed as in Step 1. The mixture was allowed to sit at 70° F. for 24 hours, and was then again filtered as in Step 1. These two steps yielded a double-treated, extra potent, repellent extract. (3) 225 ml of the double-treated extract from Step 2 was added to 14.5 fluid oz. of PLASTI DIP®. The combination was mixed thoroughly.

Ground wire from electric cable (14 AWG/2), cut at 11 cm lengths, was used in the test. The weight of wires before treated coating averaged 2.10 g. The weight of each wire after coating was between 2.7 g and 3.2 g. Six layers of protective treated coating were applied to each protected wire by repeatedly dipping the wire in the treated synthetic rubber mixture.

Untreated wires were coated with PLASTI DIP® containing no extract. Treated wires were coated with PLASTI DIP® containing double treated extract.

The treated test wires were subjected to adverse environmental effects to evaluate the durability/longevity of the protective treatment of the invention. Prior to the test, all wires were placed in a water bath (treated wires in a separate container from untreated wires) for one week. The water was exchanged at a rate of 1 gallon/minute and the water temperature was held at 18° C.

SUMMARY OF EXPERIMENTAL DESIGN AND RESULTS

Experimental Design: Small Subject, Repeated Measures

Both the treated test wires and the untreated control wires were weighed before and after their exposure to the animals, generating the data found in Table 5 for the wire corresponding to each of the five animals.

TABLE 5

(weight of wire in grams)

| | Untreated I | | Treated I | |
|---|---|---|---|---|
| | Before | After 24 hrs | Before | After 72 hrs |
| 1 | 2.73 | 2.16 | 3.20 | 3.20 |
| 2 | 2.79 | 2.13 | 3.17 | 3.17 |
| 3 | 2.81 | 2.09 | 3.08 | 3.08 |
| 4 | 2.85 | 2.13 | 3.28 | 3.28 |
| 5 | 2.84 | 2.10 | 3.15 | 3.15 |
| | Untreated wires were stripped to bare wire | | Treated wires were undamaged | |

| | Untreated II | | Treated II | |
|---|---|---|---|---|
| | Before | After 24 hrs | Before | After 72 hrs |
| 1 | 2.56 | 2.05 | 3.08 | 3.08 |
| 2 | 2.59 | 2.11 | 3.24 | 3.24 |
| 3 | 2.58 | 2.08 | 3.15 | 3.15 |
| 4 | 2.59 | 2.11 | 3.23 | 3.23 |
| 5 | 2.97 | 2.24 | 3.10 | 3.10 |
| | Untreated wires were stripped to bare wire | | Treated wires were undamaged | |

| | Untreated III | |
|---|---|---|
| | Before | After 24 hrs |
| 1 | 2.79 | 2.08 |
| 2 | 2.84 | 2.05 |
| 3 | 2.80 | 2.12 |
| 4 | 2.99 | 2.10 |
| 5 | 3.00 | 2.13 |
| | Untreated wires were stripped to bare wire | |

EXAMPLE 16

Ten rats (five of each sex, Long-Evans hooded, adult, naive) were individually caged. The males averaged 485 g in weight, and the females averaged 275 g in weight.

The test was performed in two phases. For the "Treated I" phase, two rats were exposed to wires having one level of protection, and eight rats were exposed to wires having a higher level of protection.

For rat numbers 1 and 2, 10 g of habañero powder was added to 10.1 fluid ounces (one tube) of silicone rubber (Dow Corning®, Silicone Sealant), and mixed thoroughly. For rats 3–10, 20 g of habañero powder was added to 10.1 fluid ounces of silicone rubber, and mixed thoroughly.

For "Treated II" phase, 112 grams of habañero powder was added to 600 ml of solvent (lacquer thinner) and 200 ml of denatured alcohol. The combination of three ingredients was mixed thoroughly. The mixture was filtered to separate the solids from the liquid extract. 200 ml of the extract was collected and added to 10.1 fluid ounces of silicone rubber.

Ground wire from electric cable (14 AWG/2), cut to 11-cm lengths was used in the test. The weight of wires before coating averaged 2.1 g, while the weight of wires after coating was between 4.2 g and 4.9 g. Rubber (treated and untreated) was then formed around wire using a large plastic soda straw as a mold.

After allowing one week for the silicone rubber to dry, all wires were placed in a water bath (treated wires in a separate container from untreated wires) for one week. The water was exchanged at a rate of ½ gallon/minute and the water temperature was held at 18° C.

SUMMARY OF EXPERIMENTAL DESIGN AND RESULTS

Experimental Design: Small Subject, Repeated Measures

Both the treated test wires and the untreated control wires were weighed before and after their exposure to the animals, generating the data found in Table 6 for the wire corresponding to each of the ten animals.

TABLE 6

(wire weight in grams)

| | Untreated I | | Treated I | |
|---|---|---|---|---|
| | Before | After 24 hrs) | Before | After 3 weeks |
| 1 | 4.31 | 2.17 | 4.48 | 4.37 10 g |
| 2 | 4.27 | 2.13 | 4.59 | 2.80 10 g |
| 3 | 4.23 | 2.17 | 4.32 | 4.29 20 g |
| 4 | 4.42 | 2.15 | 4.89 | 4.76 20 g |
| 5 | 4.38 | 2.23 | 4.39 | 4.39 20 g |
| 6 | 4.14 | 2.23 | 4.36 | 4.08 20 g |
| 7 | 4.40 | 2.07 | 4.92 | 3.89 20 g |
| 8 | 4.55 | 2.23 | 5.09 | 4.58 20 g |
| 9 | 4.32 | 2.13 | 4.56 | 4.57 20 g |
| 10 | 4.29 | 2.17 | 4.34 | 4.34 20 g |
| | Untreated wires were completely stripped | | | |

| | Untreated II | | Treated II (alternative formula) | |
|---|---|---|---|---|
| | Before | After 24 hrs | Before | After 3 weeks |
| 1 | 4.41 | 2.18 | 3.74 | 3.62 |
| 2 | 4.18 | 2.08 | 3.76 | 3.48 |
| 3 | 4.66 | 2.11 | 3.74 | 3.74 |
| 4 | 4.51 | 2.06 | 3.78 | 3.62 |
| 5 | 4.46 | 2.05 | 3.91 | 3.85 |
| 6 | 4.62 | 2.24 | 3.70 | 3.70 |
| 7 | 4.20 | 2.06 | 3.66 | 3.66 |
| 8 | 4.56 | 2.25 | 3.73 | 3.73 |
| 9 | 4.45 | 2.10 | 3.85 | 3.85 |
| 10 | 4.58 | 2.13 | 3.70 | 3.70 |
| | Untreated wires were completely stripped | | | |

| | Untreated III | |
|---|---|---|
| | Before | After 24 hrs |
| 1 | 4.27 | 2.06 |
| 2 | 4.31 | 2.11 |
| 3 | 4.28 | 2.09 |
| 4 | 4.51 | 2.13 |
| 5 | 4.42 | 2.15 |
| 6 | 4.29 | 2.08 |
| 7 | 4.50 | 2.06 |
| 8 | 4.40 | 2.12 |
| 9 | 4.36 | 2.11 |
| 10 | 4.46 | 2.09 |
| | Untreated wires were completely stripped | |

This example also shows how the invention may be used to provide a repellent coating whose repellent quality is substantially undiminished after repeated "wash" cycles from exposure to water.

The preceding examples can be repeated with similar success by substituting the generically or specifically described reactants and/or operating conditions of the invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. A method of repelling animals comprising the steps of:
    (a) adding habañero capsicum to at least one liquid organic solvent, wherein the habañero capsicum comprises a relative hotness greater than 50,000 Scoville units;
    (b) mixing the solvent and the capsicum and thereby extracting capsaicinoid-bearing essential oils; and
    (c) utilizing the capsaicinoid-bearing essential oils as an animal repellent.

2. The method of claim 1 wherein the adding step comprises adding a terpene oil.

3. The method of claim 1 wherein the step of adding capsicum to least one solvent comprises adding habañero to at least one solvent.

4. The method of claim 3 wherein the step of adding habañero comprises adding habañero to solvent in an amount within the range of 16 to 400 grams by weight habañero per 1000 ml of solvent.

5. A method of protecting an object from damage from animals comprising the steps of:
    (a) soaking a material in the repellent prepared in accordance with the process of claim 1; and
    (b) disposing the material about the object to be protected.

6. The method of claim 5 wherein the step of soaking a material comprises soaking a member selected from the group consisting of paper, cardboard and cloth.

7. The method of claim 1 wherein the step of mixing comprises high-speed blending for a period of time within the range of two to fifteen minutes.

8. The method of claim 1 further comprising the additional steps of:
    (a) filtering the mixed capsicum and solvent; and
    (b) collecting the resulting filtered liquid in a container.

9. A method of protecting an object from damage from animals comprising the step of applying the repellent prepared in accordance with the process of claim 8 to the surface of an object to be protected.

10. The method of claim 8 further comprising the additional steps of:
    (a) after mixing the capsicum and solvent, allowing the mixture to set for a period of time within the range from fifteen seconds to two minutes; and
    (b) stirring the mixture for a period of time within the range from fifteen seconds to three minutes before filtering the mixed capsicum and solvent.

11. The method of claim 8 wherein the step of adding capsicum to at least one solvent comprises adding habañero to at least one member selected from the group consisting of organic solvents, water, and oils.

12. The method of claim 10 wherein the step of adding habañero comprises adding habañero to solvent in an amount within the range of 16 to 400 grams by weight habañero per 1000 ml of solvent.

13. The method of claim 9 further comprising the step of maintaining the habañero and the solvent at a temperature within the range of 60° C. to 75° C. during the step of mixing the capsicum and the solvent.

14. The method of claim 13 wherein the step of mixing comprises mixing for a period of time within the range from two minutes to eight hours.

15. A method of protecting an object from damage from animals comprising the step of applying the repellent prepared in accordance with the process of claim 14 to the surface of an object to be protected.

16. The method of claim 1 additionally comprising the step of
    adding the repellent to a compatible material useful in making insulation.

17. The method of claim 16 wherein the adding habañero capsicum step comprises adding a terpene oil.

18. The method of claim 1 further comprising the step of mixing the repellent with an application vehicle.

19. The method of claim 18 wherein the step of mixing the repellent with an application vehicle comprises mixing the repellent with a member selected from the group consisting of paints, rubbers, caulks, plastics, glues, silicones, preservatives, vinyls, epoxies, resins, enamels and sealants.

20. The method of claim 18 wherein the step of mixing the repellent with an application vehicle comprises mixing the repellent with a compatible polymeric substance.

21. The method of claim 20 wherein the repellent and polymeric substance are bonded.

22. The method of claim 20 wherein the polymeric substance is natural.

23. The method of claim 20 wherein the repellent and polymeric substance are cross-linked.

24. The method of claim 20 wherein the polymeric substance is synthetic.

25. The method of claim 1 additionally comprising the step of
    adding the repellent to a compatible liquid plastic material useful in making trash bags.

26. The method of claim 25 wherein the material useful in making trash bags comprises plastic.

27. The method of claim 25 wherein the adding habañero capsicum step comprises adding a terpene oil.

28. The method of claim 25 wherein the material useful in making trash bags comprises paper.

29. The method of claim 1 wherein the step of adding capsicum to at least one solvent comprises adding capsicum to at least one member selected from the group consisting of organic solvents, water, and oils.

30. A method for preparing animal repellent comprising the steps of:
    (a) adding habañero capsicum to at least one liquid solvent, wherein the habañero capsicum comprises a relative hotness greater than 50,000 Scoville units;
    (b) blending the solvent and the capsicum for a period of tame within the range of fifteen seconds to three minutes;
    (c) allowing the blended mixture to set for a period of time within the range of fifteen seconds to two minutes;
    (d) again blending the mixture at high speed for a period of time within the range of fifteen to three minutes;
    (e) filtering the mixture to separate solids from liquid;
    (f) collecting the filtered liquid;
    (g) mixing the filtered liquid with capsicum and a solvent; and
    (h) mixing the repellent with an application vehicle comprising a compatible polymeric substance, wherein the repellent and the polymeric substance are joined by a means from the group consisting of bonding and cross-linking.

31. The method of claim 30 wherein the adding step comprises adding a terpene oil.

32. The method of claim 30 wherein the mixing step comprises mixing the filtered liquid with a terpene oil.

33. A method of protecting an object from damage from animals comprising applying the repellent prepared in accordance with the process of claim 30 to the surface of an object to be protected.

34. The method of claim 30 wherein the step of adding capsicum to at least one solvent comprises adding habañero to at least one member selected from the group consisting of organic solvents, water, and oils.

35. The method of claim 34 wherein the step of adding habañero comprises adding habañero to solvent in an amount within the range of 400 to 600 grams by weight habañero per 1000 ml of solvent.

36. The method of claim 30 further comprising the step of mixing the repellent with an application vehicle.

37. The method of claim 36 wherein the step of mixing the repellent with an application vehicle comprises mixing the repellent with a member selected from the group consisting of paints, rubbers, caulks, plastics, glues, silicones, preservatives, vinyls, epoxies, resins, enamels and sealants.

38. The method of claim 36 wherein the step of mixing the repellent with an application vehicle comprises mixing the repellent with a compatible polymeric substance.

39. The method of claim 38 wherein the polymeric substance is synthetic.

40. The method of claim 38 wherein the repellent and polymeric substance are bonded.

41. The method of claim 38 wherein the polymeric substance is natural.

42. The method of claim 38 wherein the repellent and polymeric substance are cross-linked.

43. A method of preparing a animal repellent comprising the steps of:
   (a) mixing habañero capsicum with at least one liquid solvent, wherein the habañero capsicum comprises a relative hotness greater than 50,000 Scoville units;
   (b) alternately stirring the mixture and allowing the mixture to set;
   (c) adding an additional quantity of capsicum and an additional quantity of solvent to the mixture;
   (d) again alternately stirring the mixture and allowing the mixture to set;
   (e) filtering the mixture to separate solids from a liquid;
   (f) collecting the filtered liquid;
   (g) alternately stirring the filtered liquid and allowing the filtered liquid to set; and
   (h) refiltering the filtered liquid.

44. The method of claim 43 wherein the mixing step comprises mixing a terpene oil.

45. The method of claim 43 wherein the adding step comprises adding a terpene oil.

46. The method of claim 43 wherein the step of adding an additional quantity of capsicum and an additional quantity of solvent to the mixture comprises adding an amount within the range of 50 to 150 grams habañero and an amount within the range of 150 and 250 ml of solvent to each 200 ml of mixture.

47. A method of protecting an object from damage from animals comprising the step of applying the repellent prepared in accordance with the process of claim 43 to the surface of an object to be protected.

48. The method of claim 43 wherein each step of alternately stirring the mixture and allowing the mixture to set comprises the steps of:

(a) stirring the mixture of capsicum and solvent for at least fifteen seconds;
   (b) allowing the mixture to set for at least fifteen seconds;
   (c) again stirring the mixture for at least fifteen seconds; and
   (d) allowing the mixture to set for at least fifteen seconds.

49. The method of claim 43 wherein the step of mixing capsicum with at least one liquid solvent comprises mixing an amount within the range of 400 and 600 grams by weight of habañero per 1000 ml of solvent.

50. The method of claim 43 further comprising the step of mixing the repellent with an application vehicle.

51. The method of claim 50 wherein the step of mixing the repellent with an application vehicle comprises mixing the repellent with a member selected from the group consisting of paints, rubbers, caulks, plastics, glues, silicones, preservatives, vinyls, epoxies, resins, enamels and sealants.

52. The method of claim 50 wherein the step of mixing the repellent with an application vehicle comprises mixing the repellent with a compatible polymeric substance.

53. The method of claim 52 wherein the repellent and polymeric substance are bonded.

54. The method of claim 52 wherein the polymeric substance is natural.

55. The method of claim 52 wherein the repellent and polymeric substance are cross-linked.

56. The method of claim 52 wherein the polymeric substance is synthetic.

57. A method of making an animal repellent trash bag, the method comprising the steps of:
   e) adding capsicum to at least one liquid solvent;
   f) mixing the solvent and the capsicum;
   g) filtering the resulting mixture; and
   h) adding the repellent filtrate to a compatible liquid polymeric plastic material useful in making trash bags, wherein the repellent and the polymeric material are bonded.

58. The method of claim 57 wherein the repellent and polymeric material are cross-linked.

59. The method of claim 57 wherein the polymeric material is natural.

60. The method of claim 57 wherein the polymeric material is synthetic.

61. The method of claim 57 wherein the adding step comprises adding a terpene oil.

62. A method of preparing animal repellent comprising the steps of:
   (a) adding capsicum to at least one liquid solvent;
   (b) mixing the solvent and the capsicum; and
   (c) mixing the resulting repellent with an application vehicle comprises a compatible polymeric substance, wherein the repellent and the application vehicle are bonded.

63. The method of claim 62 wherein the adding step comprises adding a terpene oil.

64. The method of claim 62 wherein the repellent and polymeric substance are cross-linked.

65. The method of claim 64 wherein the polymeric substance is natural.

66. The method of claim 64 wherein the polymeric substance is synthetic.

67. A method of preparing an animal repellent comprising the steps of:
   (a) mixing capsicum with at least one liquid solvent;
   (b) alternately stirring the mixture and allowing the mixture to set;

(c) adding an additional quantity of capsicum and an additional quantity of solvent to the mixture;

(d) again alternately stirring the mixture and allowing the mixture to set;

(e) filtering the mixture to separate solids from a liquid;

(f) collecting the filtered liquid;

(g) alternately stirring the filtered liquid and allowing the filtered liquid to set;

(h) refiltering the filtered liquid; and (i) mixing the resulting repellent with an application vehicle comprises a compatible polymeric substance, wherein the repellent and the application vehicle are bonded or cross-linked.

68. The method of claim 67 wherein the mixing capsicum step comprises mixing a terpene oil.

69. The method of claim 67 wherein the adding step comprises adding a terpene oil.

70. The method of claim 67 wherein the repellent and polymeric substance are cross-linked.

71. The method of claim 67 wherein the polymeric substance is natural.

72. A method for preparing animal repellent comprising the steps of:

(a) adding capsicum to at least one liquid solvent;

(b) blending the solvent and the capsicum for a period of time within the range of fifteen seconds to three minutes;

(c) allowing the blended mixture to set for a period of time within the range of fifteen seconds to two minutes;

(d) again blending the mixture at high speed for a period of time within the range of fifteen to three minutes;

(e) filtering the mixture to separate solids from liquid;

(f) collecting the filtered liquid; and (g) mixing the filtered liquid with capsicum and a solvent (h) mixing the resulting repellent with an application vehicle comprises a compatible polymeric substance, wherein the repellent and the application vehicle are bonded.

73. The method of claim 72 wherein the repellent and polymeric substance are cross-linked.

74. The method of claim 72 wherein the polymeric substance is natural.

75. The method of claim 72 wherein the polymeric substance is synthetic.

76. The method of claim 72 wherein the adding step comprises adding a terpene oil.

77. The method of claim 72 wherein the step of mixing the filtered liquid comprises mixing the filtered liquid with a terpene oil.

78. A method of making animal repellent insulation, the method comprising the steps of:

a) adding capsicum to at least one liquid solvent;

b) mixing the solvent and the capsicum;

c) filtering the resulting mixture; and d) adding the repellent filtrate to a compatible polymeric substance useful in making insulation, wherein the repellent and the polymeric substance are bonded.

79. The method of claim 78 wherein the repellent and polymeric substance are cross-linked.

80. The method of claim 78 wherein the polymeric substance is natural.

81. The method of claim 78 wherein the polymeric substance is synthetic.

82. The method of claim 78 wherein the adding step comprises adding a terpene oil.

83. A method of repelling animals comprising the steps of:

(a) adding habañero capsicum to at least one liquid organic solvent, wherein the habañero capsicum comprises a relative hotness greater than 50,000 Scoville units;

(b) mixing the solvent and the capsicum; and (c) mixing the repellent with an application vehicle comprising a compatible polymeric substance, wherein the repellent and polymeric substance are joined by a means from the group consisting of bonding and cross-linking.

84. A method of repelling animals comprising the steps of:

(a) adding habañero capsicum to at least one liquid organic solvent, wherein the habañero capsicum comprises a relative hotness greater than 50,000 Scoville units; and (b) mixing the solvent and the capsicum; and (c) mixing the repellent with an application vehicle comprising a compatible synthetic polymeric substance.

85. A method for repelling animals comprising the steps of:

(a) adding habañero capsicum to at least one liquid solvent, wherein the habañero capsicum comprises a relative hotness greater than 50,000 Scoville units;

(b) blending the solvent and the capsicum for a period of time within the range of fifteen seconds to three minutes;

(c) allowing the blended mixture to set for a period of time within the range of fifteen seconds to two minutes;

(d) again blending the mixture at high speed for a period of time within the range of fifteen to three minutes;

(e) filtering the mixture to separate solids from liquid;

(f) collecting the filtered liquid;

(g) mixing the filtered liquid with capsicum and a solvent; and (h) mixing the repellent with an application vehicle comprising a compatible synthetic polymeric substance.

* * * * *